(12) United States Patent  
Brits

(10) Patent No.: US 7,025,936 B1  
(45) Date of Patent: Apr. 11, 2006

(54) METHOD AND APPARATUS FOR PREPARING A SAMPLE FOR ANALYSIS OF PRECIOUS METAL CONTENT

(75) Inventor: Willem H Brits, Brakpan (ZA)

(73) Assignee: FLS Automation South Africa (Proprietary) Limited, (ZA)

( * ) Notice: Subject to any disclaimer, the term of this patent is extended or adjusted under 35 U.S.C. 154(b) by 0 days.

(21) Appl. No.: 09/830,855

(22) PCT Filed: Oct. 29, 1999

(86) PCT No.: PCT/IB99/01747

§ 371 (c)(1),  
(2), (4) Date: Apr. 27, 2001

(87) PCT Pub. No.: WO00/26664

PCT Pub. Date: May 11, 2000

(30) Foreign Application Priority Data

Oct. 29, 1998  (ZA) .................................... 98/9866  
Oct. 29, 1998  (ZA) .................................... 98/9867  
Mar. 8, 1999    (ZA) .................................... 99/1831

(51) Int. Cl.  
*B01L 3/00* (2006.01)

(52) U.S. Cl. ..................... 422/102; 422/104; 436/73; 266/230; 266/232

(58) Field of Classification Search ................. 436/26, 436/73, 80, 155, 158; 220/577; 215/12.1, 215/379; 266/227, 232; 222/591, 604; 422/102, 422/104

See application file for complete search history.

(56) References Cited

U.S. PATENT DOCUMENTS 259,282 A * 6/1882 Bavier ........................ 222/605

(Continued)

FOREIGN PATENT DOCUMENTS

GB 2289758 * 11/1995

(Continued)

OTHER PUBLICATIONS

Australia Laboratory Services, Minerals Division. "Coarse Gold Problems". vol. 7, No. 1. Jan. 1998.*

*Primary Examiner*—Jill Warden  
*Assistant Examiner*—LaToya Cross  
(74) *Attorney, Agent, or Firm*—Knobbe, Martens, Olson & Bear, LLP

(57) ABSTRACT

This invention relates to a method for assaying an ore sample to determine the concentration of gold and PGMs therein. The method comprises the steps of separating an ore sample, combining the prepared ore sample with a lead-containing flux, inductively heating the combination (typically at a pre-determined reference temperature profile) to form a fusion of slag and lead containing the gold and PGMs in the sample and separating the lead from the slag. The invention also covers a receptacle for separating molten lead from slag. The receptacle includes a base with a side wall extending from the base, the side wall defining a top-opening into the receptacle, and the side wall having a collecting cavity set into the side wall, wherein the collecting cavity is sized to collect a pre-determined amount of molten lead.

9 Claims, 4 Drawing Sheets

U.S. PATENT DOCUMENTS

| | | | |
|---|---|---|---|
| 862,008 A * | 7/1907 | Nebel | 266/165 |
| 2,479,641 A * | 8/1949 | Ripich | 266/229 |
| 3,633,780 A * | 1/1972 | Rausing | 215/12.2 |
| 4,029,302 A * | 6/1977 | Winterhager et al. | 266/204 |
| 4,113,241 A * | 9/1978 | Dore | 266/227 |
| 4,444,377 A * | 4/1984 | Groteke et al. | 266/227 |
| 5,238,485 A * | 8/1993 | Shubert | 75/421 |
| 5,472,173 A * | 12/1995 | Laszlo | 266/45 |
| 6,002,734 A * | 12/1999 | Steinman | 376/157 |

FOREIGN PATENT DOCUMENTS

KR 9105056 * 7/1991

* cited by examiner

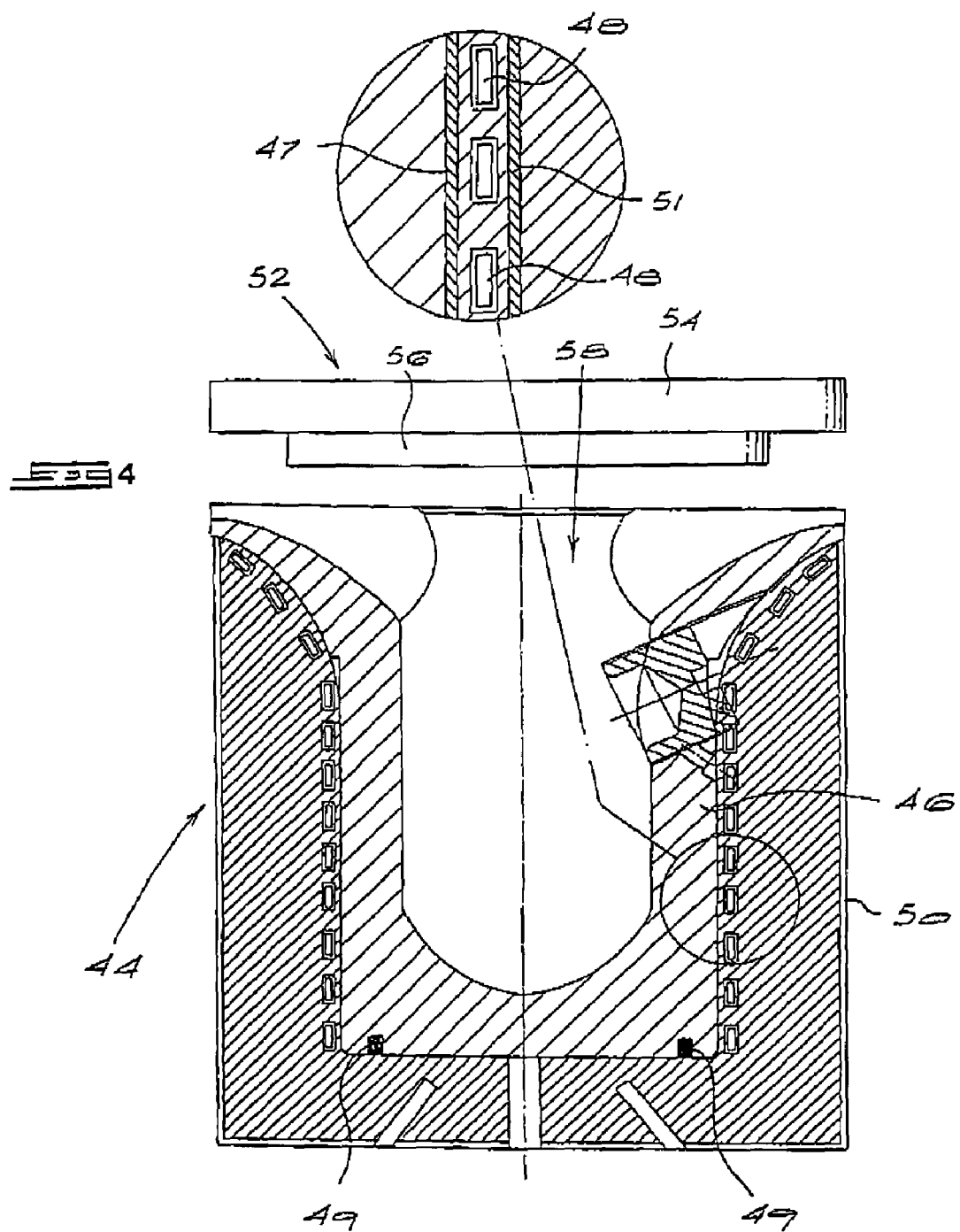

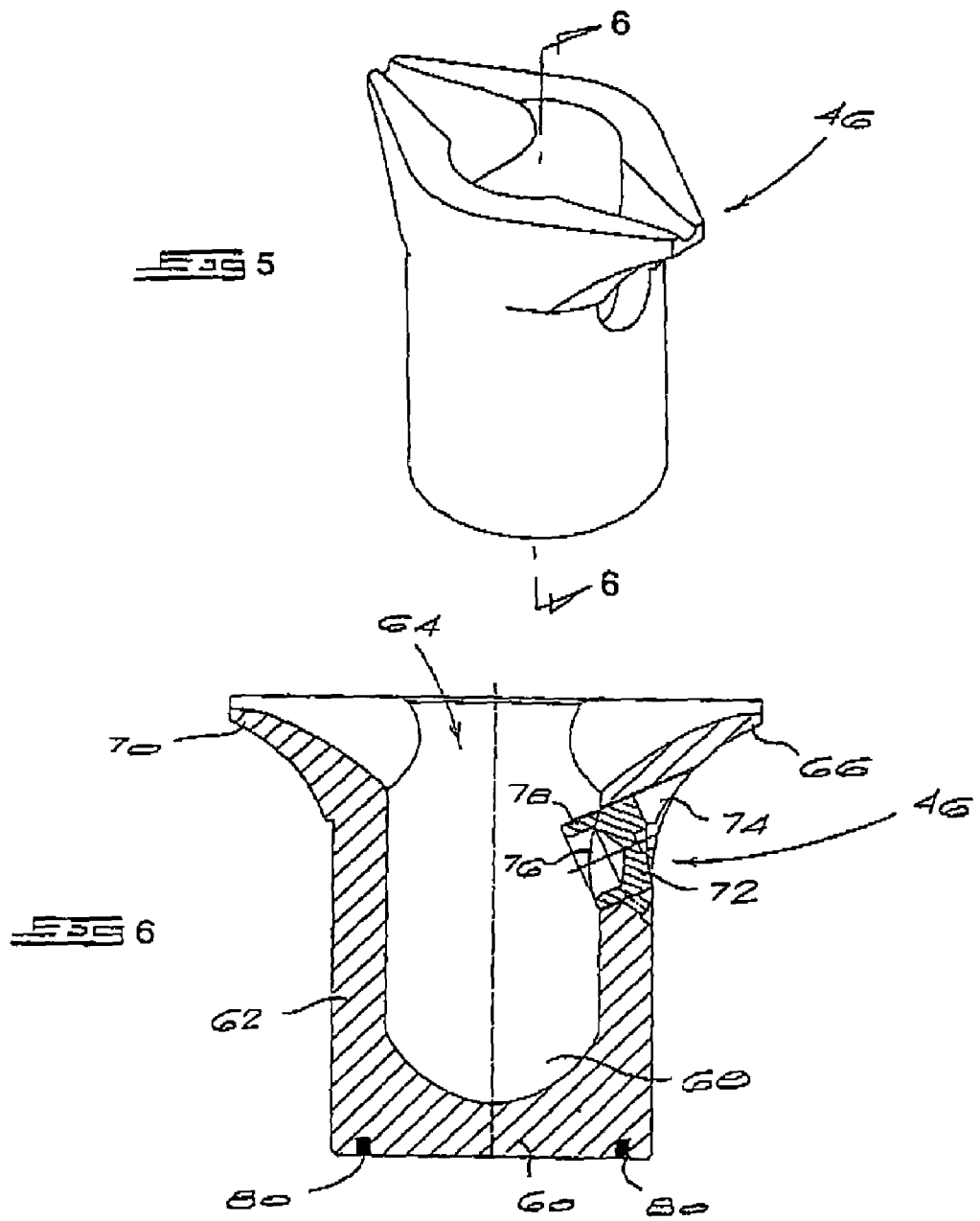

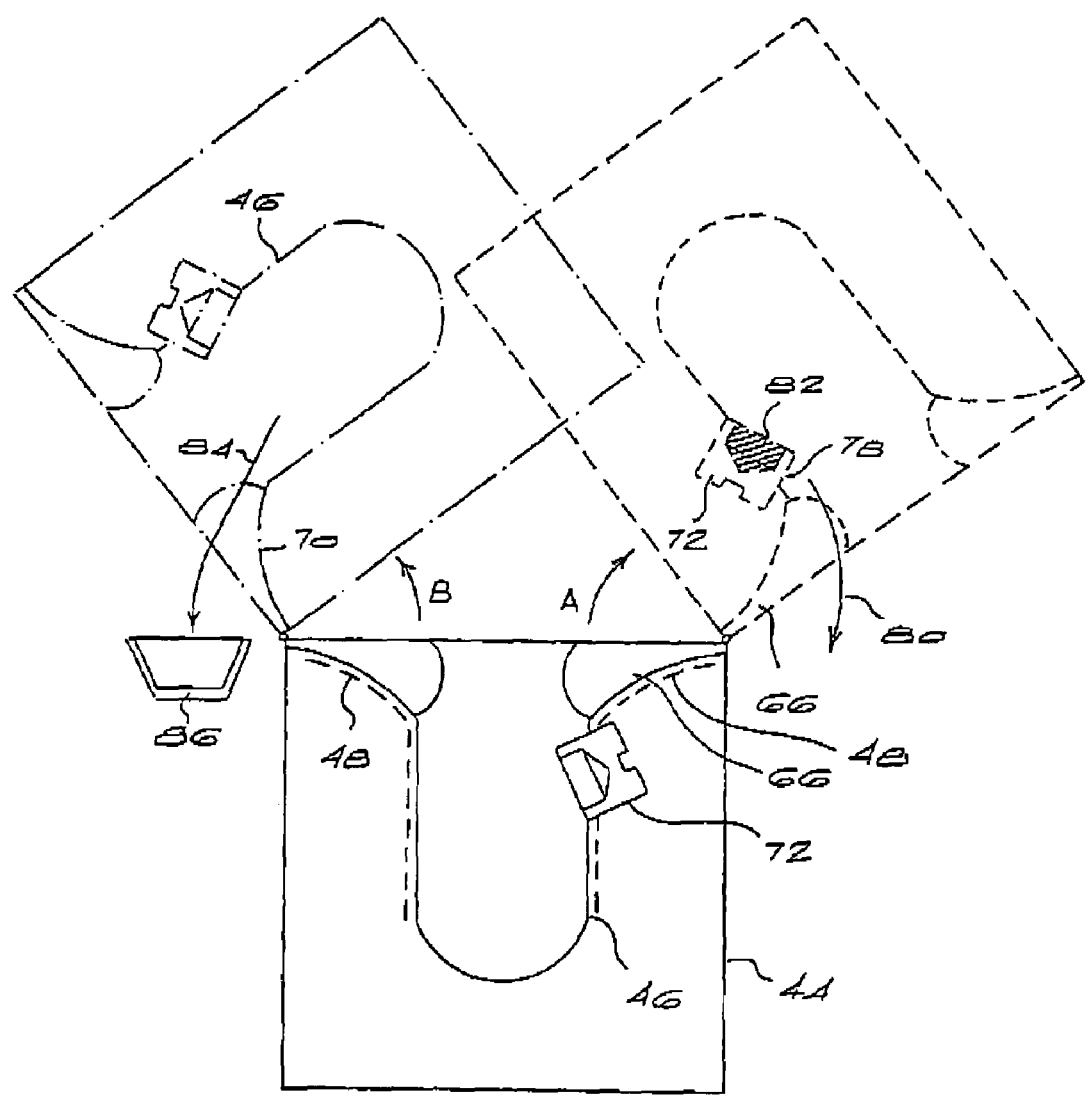

METHOD AND APPARATUS FOR PREPARING A SAMPLE FOR ANALYSIS OF PRECIOUS METAL CONTENT

This application is a national phase application under 35 U.S.C. § 371 of PCT Application Ser. No. PCT/IB99/01747 filed on Oct. 29, 1999 which claims priority to South African Application Ser. No. 98/9866 filed on Oct. 29, 1998, South African Application Ser. No. 98/9867 filed on Oct. 29, 1998 and South African Application Ser. No. 99/1831, the disclosures of which are incorporated herein by reference in their entireties.

BACKGROUND OF THE INVENTION

In order to plan and manage mining operations and to estimate recoverable ore reserves it is necessary to have the facility to determine the concentration in ore samples of precious metals, typically gold and PGMs (platinum group metals including platinum, palladium, rhodium, osmium, indium and ruthenium). It is already known to use a fire assay process for this purpose. In fire assay, PGMs and gold are separated from gangue materials by collection into either lead or nickel sulphide at temperatures of around 1200–1450° C. This is achieved by mixing an aliquot of the sample with a flux containing either lead oxide, for the lead collection, or a combination of nickel carbonate and sulphur, for the nickel sulphide, with other chemicals. A flux containing lead oxide which has been found to work satisfactorily in the conventional fire assay method consists of calcium carbonate, lead oxide, borax and silica, and a carbon source such as activated carbon, maize meal or flour. This mixture is placed into a ceramic crucible, which in turn is placed into an electric or gas fired furnace and heated to an appropriate temperature for a period of about 90 minutes. During this time the mixture melts and, because their chemical affinity, PGMs and gold are collected into either lead of nickel sulphide. On cooling the lead or nickel sulphide is separated from the gangue material and the PGMs and gold content determined by a number of analytical techniques.

The advantage of Fire Assay collection over other analytical procedures is that it effectively concentrates PGMs and gold from a large sample aliquot into a media which is much more amenable to further treatment for the separation and analysis of the PGMs and gold. Fire Assay is, therefore, used extensively in all laboratories engaged in the analysis of samples containing precious metals and, indeed, is an essential stage in the analysis of lower grade samples such as concentrates, feeds and tails.

In electrically heated, furnaces, radiant heat from resistive elements is applied to the prepared ore samples. It is difficult to maintain constant operating conditions in an electrical furnace. Furthermore, resistive elements are fragile and deteriorate over time. This variability in furnace conditions detrimentally affects the accuracy of assay results and gives rise to excessive repeat rates.

Gas fired furnaces on the other hand are noisy and require frequent maintenance, which lengthens the average time taken to complete an assay.

The flux used in assaying contains lead and is environmentally hazardous, either in dust form during the flux preparation stage, or as fumes which form during the fusion and cuppelation stages of the process. Personnel involved in the assaying process require monitoring of lead blood levels every six months, which is expensive and disconcerting to the persons involved.

The fusion pots used for fusion of the flux/ore sample combinations are brittle and break easily. In order to overcome this difficulty, each assay is duplicated or triplicated, to ensure that at least one successful assay result is obtained, which increases the overall assaying costs. Further, the duplicated or triplicated samples are fused in different furnaces in order to compensate for the variability in furnace conditions.

The recovery of lead from the fusion slag is also hazardous as the slag is broken tip, usually manually, by impact to liberate globules of lead entrapped in the slag. Slivers of slag are sharp and necessitate the wearing of adequate safety equipment. Generally, not all lead globules are usually liberated from the slag, leading to an inevitable loss of lead.

Current assay techniques are labour intensive and, therefore, prone to human error. The average time taken to complete an assay normally exceeds twelve hours. It is desired to improve the accuracy, the turnaround time and the safety aspects of known prior art assaying techniques.

SUMMARY OF INVENTION

According to a first aspect of the invention there is provided a method for assaying an ore sample to determine the concentration of selected metals therein, comprising the steps of:
preparing an ore sample;
combining the prepared ore sample with a lead-containing flux;
inductively heating the combination typically at a predetermined reference temperature profile to form a fusion of slag and lead containing the metals in the sample;
separating the lead from the slag; and
determining the concentration of the selected metals in the sample.

The predetermined reference temperature profile is determined by the characteristics and amount of the ore sample and/or the flux.

The sample may be supplied with a constant temperature profile, or it may be supplied with a varied temperature profile. For example, the sample is supplied with a high level of heat for a predetermined first period of time and then supplied with a lower level of heat for a predetermined second period of time to form the fusion of slag and lead.

The sample of ore and flux is preferably mixed in a container made from carbon-based material, and the container is inductively heated together with the sample and flux.

Preferably, the container is made from plastics material and comprises a lid which is arranged to close the container sealingly.

The container may also comprise identification means in the form of a bar code for identifying the sample contained therein.

Advantageously, the flux contains sodium hydroxide.

The sample is preferably heated inductively within a graphite or more preferably within a zirconium melting pot in an induction furnace.

Advantageously, molten lead separated from the slag is poured into a chilled mould, to provide a solid lead button.

The solid lead button may then be analyzed by way of spark analysis or laser ablation.

According to a second aspect of the invention there is provided a method as described above including the steps of storing information on each sample on a central database, providing each bottle into which the sample is poured with a unique identification means such as a bar code identifying each bottle, for example by scanning, before inserting it into the induction furnace, correlating the identity of the bottle and information on the central database, and applying a predetermined reference temperature profile to the sample, according to the information on the sample stored in the database.

Preferably, each lead button is stamped with an identification code.

According to a third aspect of the invention there is provided a receptacle or separating molten lead from slag, the receptacle comprising a base with a side wall extending from the base, the side wall defining, a top opening into the receptacle, and the side wall having a collecting cavity, wherein the collecting cavity is sized to collect a predetermined amount of molten lead.

Advantageously, the collecting cavity is located proximate the top opening of the receptacle.

Preferably, barrier means is provided between the collecting cavity and the opening of the receptacle, to trap molten lead in the collecting cavity.

The collecting cavity is preferably formed within a removable plug which is attachable to the side wall of the receptacle.

Advantageously, the receptacle includes a first spout located at the top opening above the collecting cavity.

The receptacle preferably includes a second spout located at the top opening, diametrically opposed to the first spout.

Advantageously, the receptacle is also a melting pot for an induction furnace.

The receptacle is preferably made from graphite, more preferably zirconium.

According to a fourth aspect of the invention there is provided a method for separating molten lead from slag, in the receptacle described above, the method including the steps of:

1. introducing a slag with a predetermined amount of molten lead therein into the receptacle;
2. rotating the receptacle in a first direction toward the collecting cavity so that the molten lead fills and is retained within the cavity, rotating the receptacle further so that the slag is discharged from the opening to the receptacle;
3. rotating the receptacle so that the molten lead flows out of the cavity and is discharged out of the opening to the receptacle, for example, by rotating the receptacle in a second direction, opposite to the first direction; and
4. collecting the lead discharged from the opening of the receptacle.

Advantageously, the receptacle is a melting pot surrounded by an electromagnetic coil and the electromagnetic coil is rotated together with the melting pot.

According to a fifth aspect of the invention there is provided a flux composition for use in fire assaying of ore samples, the composition containing sodium hydroxide.

Preferably, the flux composition comprises 20% to 60%, more preferably 25% to 40%, by weight, sodium hydroxide.

The composition may further comprise:

20% to 60%, preferably 25% to 40%, by weight, lead oxide; and

20% to 60%, preferably 25% to 40%, by weight, borax.

Advantageously, the composition may also comprise silver nitrate.

According to a sixth aspect of the invention, there is provided a sealed container, made from a carbon-based material, containing a charge of flux composition as described above for the fire assay of a sample of ore.

Preferably, the container includes a replaceable lid.

Typically, the container is made from a combustible material, such as a plastics material.

Advantageously, the container is made from a mixture of plastics material and a flux material, such as calcium carbonate.

Typically, the container is made from a mixture of 60 to 80%, by weight, calcium carbonate and 40 to 20%, by weight, plastics material.

BRIEF DESCRIPTION OF THE DRAWINGS

The invention will now be described in more detail, by way of example only, with reference to the accompanying drawings in which FIGS. 1 to 7 illustrate embodiments of the invention.

FIG. 1 is a schematic flow diagram of a process according to the invention for assaying an ore sample to determine the concentration of selected metals therein;

FIG. 2 is a pictorial view of a bottle containing flux;

FIG. 3 is a schematic top plan view of an apparatus according to the invention for carrying out the process of FIG. 1;

FIG. 4 is a cross-sectional view of an induction furnace according to the invention;

FIG. 5 is a pictorial view of a preferred melting pot according to the invention;

FIG. 6 is a cross-sectional view of the melting pot shown in FIG. 5, along the line 6—6; and FIG. 7 is a cross-sectional view of the induction furnace shown in FIG. 4, shown in two positions in which matter is discharged from the furnace.

DESCRIPTION OF AN EMBODIMENT

Figure 1:
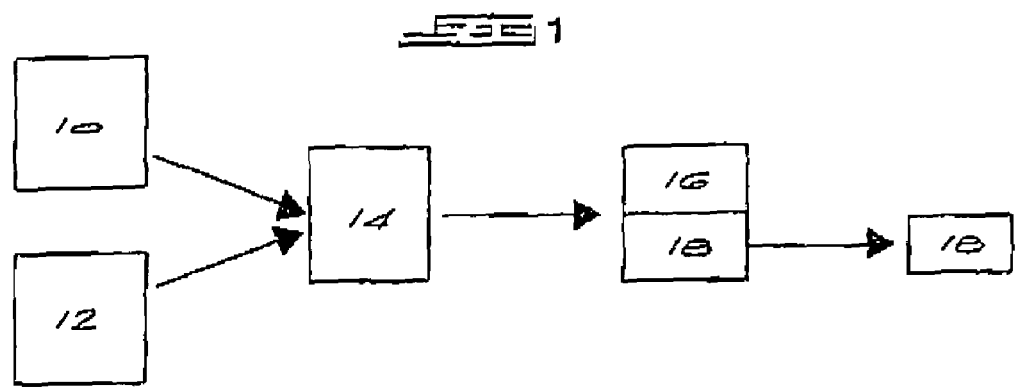

Referring to FIG. 1, according to the invention there is provided a method of assaying an ore sample, the method including the steps of preparing an ore sample 10, mixing the ore sample 10 with a flux 12 which includes lead oxide, to form a mixture 14, inductively heating the mixture 14 to form a fusion of slag 16 and lead 18 containing gold and PGMs, separating the lead 18 from the slag 16 and determining the amount of gold and PGMs in the lead.

In the sample preparation step, an ore sample is logged and its bulk weight determined. The ore sample is then dried, comminuted and sieved and split into a number of aliquots which are deposited into storage containers in the form of small plastic bottles, each of which already contains a flux.

Information on the sample, such as weight, type etc is entered onto a computer and identification means in the form of a bar code label is produced for each sample. The unused portion of the ore sample is sealed in a storage container and identified by means of a bar code label indicating identification, origin and date of assay.

Figure 2:
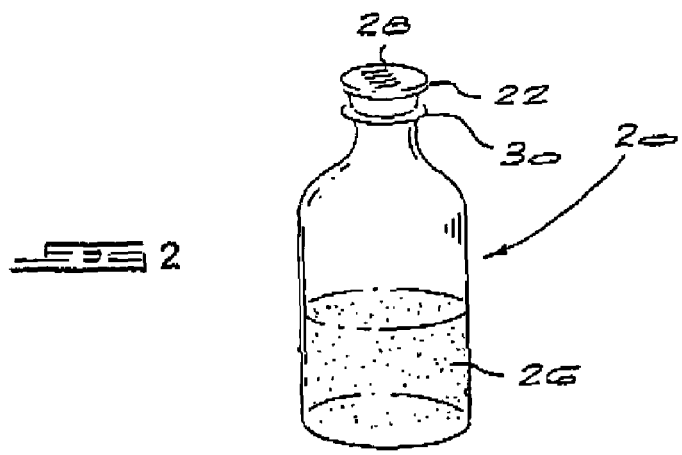

A typical bottle 20 into which an aliquot ore sample is placed is shown in FIG. 2. The bottle 20 is made from a plastics material (polypropylene) and has a lid 22 (made from polyethylene) which engages sealingly with the opening into the bottle 20. A charge of flux 26 is shown in the bottle 20. A charge of flux is a sufficient amount of a particular composition of flux for carrying out the fire assay of an aliquot of a particular ore sample. Each bottle 20 is identified by identification means in the form of a printed bar code label 28 indicative of sample identification and weight, which is attached to the top surface of the lid 22. The bottle is also provided with a ridge 30 just below the lid 22.

In a preferred embodiment of the invention the bottle 20 is made from a mixture of plastics material (such as polypropylene) and a flux material. The bottle typically comprises 60 to 80% calcium carbonate and 40 to 20% polypropylene. The advantages of including flux with the plastics material is discussed below.

The flux 26 comprises:
20% to 60%, preferably 25% to 40%, by weight, sodium hydroxide (NaOH);
20% to 60% preferably 25% to 40%, by weight, lead oxide;
20% to 60%, preferably 25% to 40%, by weight, borax; and
may also contain a small amount (O to 1%) of silver nitrate.

Each bottle 20 contains a predetermined charge and constitution of flux. The bottles are conveniently filled with flux on a production line at a production site and then transported to the site at which assaying takes place. The charge of flux, which varies from 200 to 450 g, depends on the amount and type of sample being assayed. Generally, there is a ratio of flux to sample of 4:1 to 6.1, by weight. The constitution of the flux depends on the characteristics of the sample being assayed. For example, a higher amount of borax is added for samples containing higher concentrations of base metals and a higher amount of sodium hydroxide is added for samples containing high amounts of silicates.

It is important that the lid 22 engages sealingly with the opening to the bottle 20 to ensure that the sodium hydroxide (NaOH) which is corrosive and hygroscopic does not come into contact with the atmosphere during transportation and storage of the bottle and flux.

In the process, the lid 28 of the bottle 20 is removed an aliquot sample of ore is added to a bottle 20 containing flux 26, the lid 28 is applied back onto the bottle 20 and the sample and flux is combined by merely shaking the bottle.

Previously, mixing containers were used which caused spillages and contamination between samples. Thus, the bottle 20 conveniently provides a package containing a required charge of flux which is also used to combine the aliquot sample and the flux.

It is envisaged that the sample preparation step is automated as a series of mechanically linked steps, enabling the preparation of an ore sample for assaying without the need for manual intervention.

Figure 3:
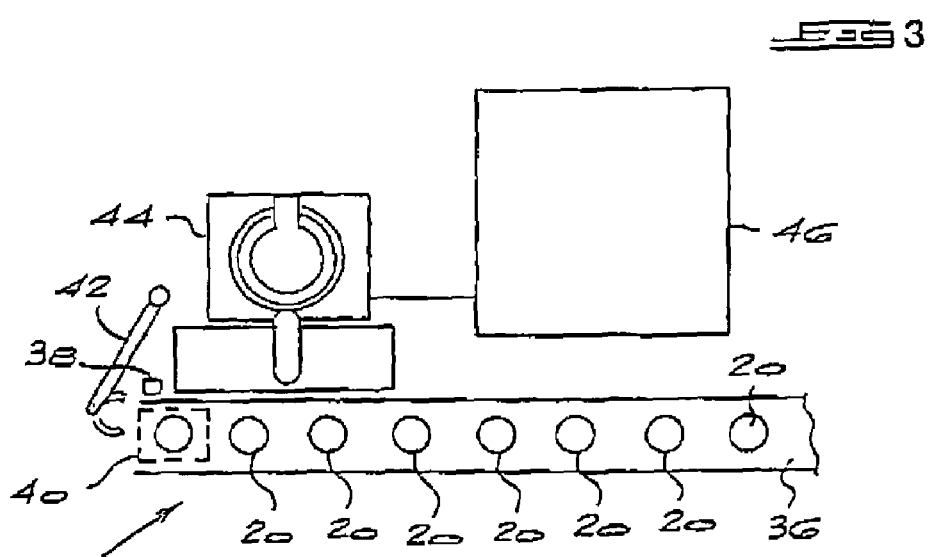

Referring to FIG. 3, bottles 20 which contain ore sample combined with flux are loaded onto a sample loader 34 which comprises a conveyor belt 36, an optical sensor 38, a bar code reader 40, and a mechanical gripper arm 42. In use, the optical sensor 38 senses the presence of a bottle 20, the bar code reader 40 (positioned above the bottle, and shown in dotted outline) scans the bar code 28 on the lid of the bottle 20 and the gripper arm 42 grips the bottle at the ridge 30 and transfers it into an induction furnace 44 which is powered by a generator 46. The conveyor 36 conveys the next bottle 20 in line with the sensor 38 and this next bottle is then ready to be transferred into the induction furnace 44. Once placed in the induction furnace 44, the identity of the bottle 20 is compared to the information stored on the central database and the bottle 20 is heated at a temperature profile that corresponds to the ore sample and flux contained within the bottle 20.

Referring to FIG. 4, the induction furnace 44 includes a removable melting pot 46 for melting the sample and flux. The melting pot 46 may be made from any material that can sustain temperatures of up to 1500° C. and which is not adversely affected by electromagnetic waves from an induction coil. For example, graphite or zirconium may be used. Zirconium is preferred because it is resistant to sodium hydroxide fusions and does not oxidise as readily as graphite at high temperatures. Zirconium also has a high melting point of 1850° C., well above the operation temperatures of the induction furnace. It is important that the temperature of the melting pot 46 is monitored and thermocouples 49 are provided on the melting pot 46 for this purpose. The melting pot 46 is surrounded by a barrier 47 of ceramic material (1600 heat isolating) which in turn is surrounded by an induction coil 48. The induction coil 48 is surrounded by a shunt 51 that directs electromagnetic waves from the coil 48 toward the melting pot 46. The abovementioned components are housed in a housing 50 which is made from a ceramic material (polyester board GPO3). The furnace 44 also has a lid 52 which has a backing 54 also made from the ceramic material and an underside 56, made from alumina or zirconia based ceramic material, which closes the opening 58 into the melting pot 46, when the lid 52 is closed. It is important that the lid 52 closes the melting pot 46 sufficiently to create a reducing atmosphere therein to minimize oxidation of, the melting pot 46 at the high temperatures within the furnace.

Once a bottle 20 has been inserted into the melting pot 46 the lid 52 is closed, and the bottle 20 and mixture of sample and flux therein are heated according to a predetermined temperature profile which is controlled by the amount of power applied to the induction coil. The temperature profile may be selected according to the amount and characteristics of ore which is being assayed and also the amount and characteristics of the flux 26.

In a typical example where the temperature profile is kept constant, the melting pot 26 is heated to about 900° and the flux and sample is inserted into the melting pot 26. The coil 48 is supplied with 15–30 kW of electrical energy from the generator 48 for a predetermined first period of time (usually 20 to 30 seconds) to heat the pot to about 1250° C. and then dropped to 10 to 12 kW for a predetermined second period of time (usually 20 to 30 seconds), maintaining the temperature of the melting pot at about 1250° C. Thus, fusion of the ore and flux takes from 45 to 90 seconds, generally approximately 60 seconds.

If necessary, the sample and flux may be heated at a predetermined varied temperature profile, for example by first heating the flux and sample to about 1250° C. for a first period of time (20–30 seconds) to melt the sample and flux and to then decrease the temperature to about 1000° C. for a second period of time (20–30 seconds), while the gold and PGMs are collected by the lead.

Another important aspect of the invention is that the temperature profile applied to each sample can be computer-controlled and thus the heating conditions can be accurately controlled, according to the identification made by the bar code reader. Information on each sample, such as sample type, sample weight, flux weight, flux composition, fusion conditions (i.e. temperature profile) is stored on a central database. Each sample is identified before it is added to the furnace and it is then heated according to a predetermined temperature profile. The system can also be used to subject similar ores, or ores from the same area, to similar or the same conditions, to ensure consistent assay results.

Fusion of the ore and flux is extremely quick and the alternating electro-magnetic waves (eddy waves) from the induction coil causes a violent stirring action of molten lead within the crucible which results in complete collection of gold and PGMs by the lead within about 60 seconds of power being applied to the induction furnace.

During heating, the temperature of the melting pot must be monitored by the thermocouples 49 and by altering the energy applied to the induction coil 48 to ensure that the temperature of the molten lead and flux remains within a preferred temperature range of between 1150° C. and 1300° C. If the temperature exceeds 1450° C. chrome III within the sample will be converted to chrome V and the chrome metal formed can trap gold and PGM's and negatively affect results. If the temperature drops too low (below 900° C.), the slag will begin to solidify and it is then difficult to separate the slag from the lead.

The ceramic housing 50 ensures that, while the temperature within the crucible 46 can reach up to 1400° C., the outer surface of the ceramic housing 50 does not reach more that 60 to 100° C. This is because the ceramic housing 50 is not heated by eddy waves from the induction coil 48. The ceramic barrier 47 (which is not heated by the induction coil) serves to insulate the crucible 46 so that radiant energy is isolated within the crucible.

The advantage of the flux 26 over known flux compositions is that the sodium hydroxide has a melting point of 318° C., which is much lower than the melting point of CaCO3, used in conventional fire assay processes. Thus, when the flux 26 is added to the crucible 46 in the induction furnace 46 (which is normally preheated a temperature of about 1000° C.), the sodium hydroxide melts, wets the sample and flux, and retards spattering and boiling when power is applied to the induction furnace. The sodium hydroxide then reacts with silicates in the sample to form slag. Up to now it has not been possible to use sodium hydroxide in conventional fire assay processes as these processes make use of clay pots and the sodium hydroxide would react with silica in the pots and destroy them during heating. The sodium hydroxide does not however have this effect on a graphite or zirconium melting pot 46. Also, there has been no feasible way of storing and transporting NaOH, because it is hygroscopic, and the sealed containers address this problem. Furthermore, fire assay flux used in the past containing calcium carbonate cannot be used in an induction furnace as it will blow out during rapid heating of the melting pot 46.

Thus, the flux 26, comprising sodium hydroxide makes it possible to rapidly melt an ore sample in an induction furnace as described above without losing flux and ore sample in the process.

The plastics bottle 20 is also an important part of the heating process as it provides a carbon source for reducing the lead oxide to produce molten lead. The inclusion of flux (calcium carbonate) with the plastic is to replace excess plastic which is merely burnt away, and to reduce flames and smoke during heating.

Referring back to FIG. 3, after the sample has been heated in the induction furnace 44, the molten sample, which comprises lead containing gold and PGM's from the sample, and slag, is separated.

The mixture of slag and lead may be poured from the melting pot 46 into another receptacle and the lead and slage separated in that receptacle. However, according to a preferred embodiment of the invention, the melting pot 46 also performs the function of separating the molten lead from the slag.

FIG. 5 shows a melting pot 46 which is arranged to be received in an induction furnace, mid which serves the dual purpose of separating molten lead from slag. As discussed above, the melting pot 46 may be made from a material such as graphite or zirconium. Zirconium is preferred as molten lead does not adhere to the heated zirconium. This is advantageous as the melting pot 46 is intended to be used for numerous samples and this limits the contamination of subsequent samples from previous samples.

Referring to FIG. 6 the melting pot 46 comprises a base 60 with a side wall 62 extending from the base and defining a top opening 64. A first spout 66 is provided at the top opening 64 for decanting molten material from a melting zone 68 within the melting pot 46. A second spout 70 is provided at the top opening 64 and is diametrically opposed to the first spout 66.

A collector 72 defining a collecting cavity 76 is provided on the side wall 62 of the melting pot 46, below the first pouring spout 66. The collector 72 may be formed integrally with the pot but is preferably removable in the form of an externally threaded plug which screws into a complimentary threaded aperture 74 in the side wall 62. The collecting cavity 76 is sized to accommodate only a predetermined amount of molten lead (i.e. the amount of lead in a molten assay sample). In a typical example, the collecting cavity 76 is sized to accommodate only 64 grams of lead from a flux containing 70 grams of lead oxide. Depending on the amount of lead in a molten sample the cavity 76 may be selected to contain from 35 to 110 grams of lead. The removable plug is advantageous as different size collecting cavities 76 can be selected and provided for different samples that are being assayed. This is important as the zirconium melting pot 46 is expensive to manufacture. The collector 72 is located proximate the top opening 64, and away from the melting zone 68, where the pot is corroded during fusion, so that the collector is not damaged during fusion.

In addition to what is stated above, the plug 72 has a side wall 78 which protrudes from the side wall 62 of the side wall 62 of the melting pot 46. The side wall 78 is advantageous as it provides a barrier that helps to collect lead in the collecting cavity 76.

As mentioned above, it is important to monitor the temperature of the melting pot 46 during operation and thermocouples 80 are provided in the base 60 of the melting pot 46, for this purpose.

Once the sample and flux have been fused to provide a slag and when the gold and PGM's have been collected in the molten lead, the molten lead and slag are separated by rotating the melting pot 46 to tip firstly the slag and then secondly and separately the lead from the melting pot 46. In this embodiment of the invention the melting head is not removed from the furnace and separation is conveniently achieved by tipping the whole of the induction furnace, i.e. tipping the induction coil together with the melting pot 46.

Referring to FIG. 7, after a sample and flux have been fused, in a melting pot 46 in an induction furnace 44, the furnace 44 is rotated in a first direction "A" toward the first spout 66 and the lead collector 72. The furnace 44 is rotated through approximately 160°. Because of different densities and viscosities, slag 80 is poured out of the melting pot 46 via the first spout 66 and all of the molten lead 82 is trapped in the lead collector 72. The side wall 78 of the collector 72 forms a barrier that protrudes from the side wall of the melting pot 46 and assists in the collection of the molten lead.

The slog that is poured out of the melting pot 46 is poured into a waste bin (not shown). After all of the slag has discharged from the melting pot 46, the furnace is rotated back into an upright position.

The furnace 44 is then rotated in a second direction "B" which is opposite to the first direction "A", also through about 160°. Molten lead 84 within the melting pot 46 is then discharged out of the melting pot 46, via the second spout 70 into a water-cooled mould 86.

It is important to keep the melting head 46 at a temperature above 900° C. during the above process so that the molten lead and slag are properly separated and so that molten lead is not left behind within the melting head 46. In this regard, the induction coil 48 extends to the spouts 68 and 70 to heat them and ensure that they do not cool to below 900° C.

The mould 86 is water-cooled to about 10° C. and the molten lead poured into the mould solidifies within about 5 to 10 seconds to form a lead button.

Rapid cooling of the molten lead stops gold and PGMs in the lead from forming layers ensuring that ite concentration of gold and PGMs within the lead button is homogenous.

Thereafter, the button is removed from the mould and stamped with an identification number which corresponds to the bar code which was read at the beginning of the process and the buttons are stored on a button storage rack, ready to be analyzed.

The amount of gold and PGMs within the button may be analysed by any conventional processes, for example by cupellation or lead dissolution. The lead cupellation processes takes approximately 2.5 hours to perform and the lead dissolution process takes approximately 8 hours to perform. The main advantage of homogenous button 74 produced by the process of the invention is that it can be analysed by way of much quicker processes such as spark analysis and laser ablation. In prior art processes, due to the separation and cooling techniques employed, PGMs and gold form layers within the lead and the lead cannot be analysed by spark analysis or laser beam ablation. As spark analysis and laser ablation only takes approximately 30 seconds, the use of these processes on the lead buttons produced by the invention dramatically reduces the time taken up by analysis. By using spark analysis or laser ablation, the whole fire assay and analysis process could be done in far less time than the twelve hour turn around time of known processes.

In addition to the above advantages, the fire assay method and apparatus according to the invention provides a much more comfortable working environment than the hot and uncomfortable working environment of prior art furnaces. The apparatus according to the invention also takes up far less work space and means that assay laboratories are more financially viable. Furthermore, the system requires less power than prior an processes and reduces replacement parts such as elements, clamps and braids for furnaces, loading and pouring equipment and clay crucibles. Lastly, the apparatus and process of the invention can provide an automated process that is not labour intensive.

EXAMPLE 1

A typical charge of flux according to the invention for analyzing 5 g concentrate ore samples from a reef in Rustenburg in South Africa, to test for platinum, palladium, rhodium and gold has the following amount and composition:
80 g Borax
85 g Litharge
45 g NaOH The flux is provided in a sealed plastic bottle. The bottle has a receptacle portion that weighs from 35 to 45 g and a lid that weighs ±10 g. The lid is made from polyethylene and the receptacle is made from 40%, by weight, polypropylene and 60%, by weight, calcium carbonate.

EXAMPLE 2

A typical charge of flux according to the invention for analyzing 75 g feed ore samples from a reef in Rustenburg in South Africa, to test for platinum, palladium, rhodium and gold has the following amount and composition:
80 g Borax
85 g Litharge
60 g NaOH The flux is provided in a sealed plastic bottle. The bottle has a receptacle portion that weighs from 50 to 60 g and a lid that weighs ±10 g. The lid is made from polyethylene and the receptacle is made from 40%, by weight, polypropylene and 60%, by weight, calcium carbonate.

EXAMPLE 3

A typical charge of flux according to the invention for analyzing 100 g tail ore samples from a reef Rustenburg in South Africa, to test for platinum, palladium, rhodium and gold has the following amount and composition:
160 g Borax
85 g Litharge
140 g NaOH The flux is provided in a sealed plastic bottle. The bottle has a receptacle portion that weighs from 60 to 75 g and a lid that weighs 10 g. The lid is made from polyethylene and the receptacle is made from 40%, by weight, polypropylene and 60%, by weight, calcium carbonate.

EXAMPLE 4

This example shows a typical method according to the invention, in which feed ore samples from a mine in Rustenburg, South Africa, were analyzed. Feed ore samples were prepared by drying feed tail ore, comminuting and sieving it, and weighing aliquot samples of 75 g of ore.

The lid of a sealed container as described in Example 2 and containing a flux composition according to Example 2 was opened. An aliquot ore sample was added to the container and the lid was replaced. The container was then shaken to combine the ore sample and the flux composition.

The container was then inserted into a triple pitch impregnated graphite pot which was surrounded by an induction coil in an induction furnace. The induction coil was powered by a 15 kW induction generator.

The graphite pot had been pre-heated to 1250° C. Once the bottle had been inserted into the melting pot, the lid of the furnace was closed and the heat of the pot was maintained at 1250° C. for 90 seconds, by applying 15 kW of power to the coil at 6.5 kH. Although it is possible and sometimes advantageous to heat the sample according to a varied temperature profile, the temperature in this example was kept constant at 1250° C. during melting and fusion.

After 90 seconds the power to the induction furnace was reduced and the molten sample of lead, and slag were poured into and separated in a heated separator as described in South African provisional patent application no. 99/1831 which is incorporated herein by reference.

The separated molten lead was poured into a chilled mould and formed into a solid lead button within 10 seconds.

The above process was carried out with 10 aliquot samples of ore. The solid lead buttons were then analyzed by cupellation and lead dissolution methods and the results of the analysis are set out in Table 1 below:

TABLE 1

| | Induction | | | | | | | | | |
|---|---|---|---|---|---|---|---|---|---|---|
| | Lead dissolution | | | | | Cupellation | | | | |
| | Pt | Pd | Rh | Au | 4T | Pt | Pd | Rh | Au | 4T |
| | 2.03 | 2.28 | 0.198 | 0.293 | 4.80 | 2.32 | 2.42 | 0.188 | 0.380 | 5.31 |
| | 2.17 | 2.37 | 0.198 | 0.285 | 5.02 | 2.25 | 2.27 | 0.188 | 0.275 | 4.98 |
| | 2.03 | 2.33 | 0.198 | 0.280 | 4.84 | 2.15 | 2.26 | 0.188 | 0.258 | 4.86 |
| | 2.14 | 2.27 | 0.193 | 0.283 | 4.89 | 2.1 | 2.34 | 0.188 | 0.300 | 4.93 |
| | 2.12 | 2.38 | 0.195 | 0.278 | 4.97 | 2.08 | 2.28 | 0.180 | 0.275 | 4.82 |
| | 2.17 | 2.39 | 0.193 | 0.285 | 5.04 | 2.41 | 2.32 | 0.180 | 0.298 | 5.21 |
| | 2.37 | 2.25 | 0.185 | 0.343 | 5.15 | 2.02 | 2.29 | 0.190 | 0.333 | 4.83 |
| | 2.07 | 2.33 | 0.198 | 0.233 | 4.83 | 2.23 | 2.4 | 0.193 | 0.268 | 5.09 |
| | 2.20 | 2.41 | 0.203 | 0.293 | 5.11 | 2.07 | 2.31 | 0.185 | 0.268 | 4.83 |
| | 2.13 | 2.27 | 0.190 | 0.343 | 4.93 | 2.07 | 2.25 | 0.190 | 0.275 | 4.79 |
| Avg | 2.14 | 2.33 | 0.195 | 0.292 | 4.96 | 2.17 | 2.31 | 0.19 | 0.29 | 4.96 |
| % RSD | 4.4 | 2.4 | 2.5 | 10.4 | 2.3 | 5.6 | 2.4 | 2.1 | 12.2 | 3.5 |
| NiS Consensus | 2.10 | 2.31 | 0.208 | 0.248 | 4.86 | 2.10 | 2.31 | 0.206 | 0.246 | 4.66 |

The same feed sample was in a nickel sulphide fire assay process known in the prior art. The results of these tests are set out in Table 2 below:

TABLE 2

| | Fire Assay | | | | | | | | | |
|---|---|---|---|---|---|---|---|---|---|---|
| | Lead dissolution | | | | | Cupellation | | | | |
| | Pt | Pd | Rh | Au | 4T | Pt | Pd | Rh | Au | 4T |
| | 1.57 | 1.73 | 0.140 | 0.270 | 3.71 | 1.87 | 1.75 | 0.135 | 0.190 | 3.95 |
| | 2.14 | 1.94 | 0.160 | 0.260 | 4.50 | 1.73 | 1.78 | 0.140 | 0.200 | 3.85 |
| | 1.66 | 1.71 | 0.150 | 0.250 | 3.77 | 1.77 | 1.88 | 0.145 | 0.185 | 3.96 |
| | 1.84 | 1.96 | 0.160 | 0.220 | 4.18 | 1.98 | 1.99 | 0.153 | 0.260 | 4.38 |
| | 2.08 | 2.11 | 0.190 | 0.250 | 4.63 | 2.39 | 2.21 | 0.170 | 0.288 | 5.06 |
| | 2.03 | 2.14 | 0.180 | 0.280 | 4.63 | 1.97 | 2.01 | 0.158 | 0.318 | 4.45 |
| | 1.94 | 2.05 | 0.180 | 0.460 | 4.63 | 1.97 | 2.15 | 0.163 | 0.260 | 4.54 |
| | 2.07 | 2.14 | 0.190 | 0.230 | 4.63 | 1.96 | 2.25 | 0.173 | 0.250 | 4.63 |
| | 2.03 | 2.21 | 0.180 | 0.300 | 4.72 | 2.37 | 2.3 | 0.170 | 0.260 | 5.10 |
| | 2.23 | 2.32 | 0.200 | 0.280 | 5.03 | 2.23 | 2.2 | 0.180 | 0.253 | 4.66 |
| Avg | 1.96 | 2.03 | 0.173 | 0.280 | 4.44 | 2.02 | 2.05 | 0.159 | 0.246 | 4.48 |
| % RSD | 10.2 | 9.2 | 10.7 | 22.9 | 9.1 | 10.9 | 9.3 | 9.1 | 16.5 | 9.6 |
| NiS Consensus | 2.10 | 2.31 | 0.208 | 0.246 | 4.86 | 2.10 | 2.31 | 0.208 | 0.246 | 4.86 |

From Tables 1 and 2 it is clear that the results of the lead buttons prepared in the induction heating process according to the invention compare very well with the results the lead buttons prepared by the nickel sulphide fire assay process. In fact, the RSD for the induction process is significantly lower than that of the nickel sulphide fire assay process.

EXAMPLE 5

Lead buttons from an ore sample, prepared by a process according to the invention as described in Example 4 were tested by spark analysis and were found to provide accurate results.

A tail sample from a reef in Rustenburg South African was treated in the same way as described in Example 4 to produce three lead buttons. The buttons were analysed by spark analysis and the results are set out below:

| Pt | Pd | Rh | Au | Total PGM |
|---|---|---|---|---|
| 0.53 | 0.20 | 0.07 | 0.07 | 0.87 |
| 0.54 | 0.19 | 0.06 | 0.04 | 0.83 |
| 0.55 | 0.19 | 0.06 | 0.04 | 0.84 |

Conventional cupellation techniques were carried out on lead buttons from the same sample and revealed a total PGM value of 0.82 grams per ton.

EXAMPLE 6

The process according to the invention as described in Example 4 was carried out using a melting pot made of zirconium, except the ore sample was replaced with silica. After fusion, it was found that the zirconium melting, pot is superior to the graphite melting pot in that it did not oxidise as much at high temperatures as the graphite pot, and the molten lead does not adhere as much to the zirconium pot.

What is claimed is:

1. A receptacle for separating molten lead from slag, the receptacle comprising a base with a side wall extending from the base, the side wall defining a melting zone cavity having a top opening into the receptacle, and the side wall having a collecting cavity set into the side wall and having a separate opening within the side wall, wherein said collecting cavity comprises a cavity within the melting zone cavity, wherein the collecting cavity is sized to collect a predetermined amount of molten lead.

2. A receptacle according to claim 1 wherein the collecting cavity is located proximate the top opening of the receptacle.

3. A receptacle according to claim 1 wherein barrier means is provided between the collecting cavity and the opening of the receptacle, to trap molten lead in the collecting cavity.

4. A receptacle according to claim 1 wherein the collecting cavity is formed within a removable plug which is attachable to the side wall of the receptacle.

5. A receptacle according to claim 1 including a first spout located at the top opening, above the collecting cavity.

6. A receptacle according to claim 5 including a second spout located at the top opening, diametrically opposed to the first spout.

7. A receptacle according to claim 1 wherein the receptacle is also a melting pot for an induction furnace.

8. A method of separating molten lead from slag, in the receptacle of claim 1, the method including the steps of:
   (1) introducing a slag with a predetermined amount of molten lead therein into the receptacle;
   (2) tug the receptacle in a first direction toward the collecting cavity so that the molten lead fills and is retained within the cavity, and turning the receptacle further so that the slag is discharged from the opening;
   (3) turning the receptacle in a second direction so that the molten lead flows out of the collecting cavity,
   (4) tug the receptacle further so that the molten lead flows out of the opening; and
   (5) collecting the lead discharged from the opening.

9. A receptacle for separating molten lead from slag, the receptacle comprising a base with a side wall extending from the base, the side wall defining a melting zone cavity having a top opening into the receptacle, and the side wall having a collecting cavity set into the side wall, wherein said collecting cavity comprises a cavity within the melting zone cavity, wherein the collecting cavity is sized to collect a predetermined amount of molten lead, wherein the collecting cavity is formed within a removable plug which is attachable to the side wall of the receptacle.

\* \* \* \* \*

UNITED STATES PATENT AND TRADEMARK OFFICE
CERTIFICATE OF CORRECTION

PATENT NO.         : 7,025,936 B1
APPLICATION NO. : 09/830855
DATED               : April 11, 2006
INVENTOR(S)       : Willem H. Brits It is certified that error appears in the above-identified patent and that said Letters Patent is hereby corrected as shown below:

In column 1, line 38, delete "of" and insert --or--, therefore.

In column 1, line 51, after "heated" delete ",".

In column 1, line 64, delete "cuppelation" and insert --cupellation--, therefore.

In column 2, line 10, delete "tip," and insert --up,--, therefore.

In column 3, line 10, after "receptacle" delete "or" and insert --for--, therefore.

In column 5, line 14, delete "(O" and insert --(0--, therefore.

In column 5, line 22, delete "6.1," and insert --6:1,--, therefore.

In column 6, line 21, after "oxidation of" delete ",".

In column 6, line 35 (approx.), delete "48 for" and insert --46 for--, therefore.

In column 7, line 53, delete "theinduction" and insert --the induction--, therefore.

In column 7, line 57, delete "slage" and insert --slag--, therefore.

In column 7, line 63, delete "mid" and insert --and--, therefore.

In column 8, line 61, delete "slog" and insert --slag--, therefore.

In column 9, line 14, delete "ite" and insert --the--, therefore.

In column 9, line 46 (approx.), delete "an" and insert --art--, therefore.

In column 10, line 28 (approx.) delete "10 g" and insert -- ±10 g--, therefore.

In columns 11-12 (Table 1), line 18 (approx.), delete "0.248" and insert --0.246--, therefore.

In columns 11-12 (Table 1), line 18 (approx.), delete "0.206" and insert --0.208--, therefore.

In columns 11-12 (Table 1), line 18 (approx.), delete "4.66" and insert --4.86--, therefore.

UNITED STATES PATENT AND TRADEMARK OFFICE
CERTIFICATE OF CORRECTION

PATENT NO. : 7,025,936 B1
APPLICATION NO. : 09/830855
DATED : April 11, 2006
INVENTOR(S) : Willem H. Brits It is certified that error appears in the above-identified patent and that said Letters Patent is hereby corrected as shown below:

In column 11, line 21, after "was" insert --tested--.

In columns 11-12 (Table 2), line 6, delete "1.88" and insert --1.86--, therefore.

In columns 11-12 (Table 2), line 9, delete "4.45" and insert --4.46--, therefore.

In columns 11-12 (Table 2), line 13, delete "4.66" and insert --4.86--, therefore.

In column 13, line 19, in claim 8, delete "tug" and insert --turning--, therefore.

In column 14, line 4, in claim 8, after "cavity" delete "," and insert --;--, therefore.

In column 14, line 5, in claim 8, delete "tug" and insert --turning--, therefore.

Signed and Sealed this

Fourteenth Day of November, 2006

JON W. DUDAS
*Director of the United States Patent and Trademark Office*